(12) United States Patent
Head et al.

(10) Patent No.: US 11,257,573 B2
(45) Date of Patent: Feb. 22, 2022

(54) SYSTEM FOR ADJUSTING AN AUDIO/VISUAL DEVICE BASED ON HEALTH AND WELLNESS DATA

(71) Applicant: Disney Enterprises, Inc., Burbank, CA (US)

(72) Inventors: Gregory Head, Los Angeles, CA (US); Lee Bombard, Acton, CA (US); Yazmaliza Yaacob, Burbank, CA (US)

(73) Assignee: Disney Enterprises, Inc., Burbank, CA (US)

( * ) Notice: Subject to any disclaimer, the term of this patent is extended or adjusted under 35 U.S.C. 154(b) by 484 days.

(21) Appl. No.: 15/678,992

(22) Filed: Aug. 16, 2017

(65) Prior Publication Data

US 2019/0057187 A1 Feb. 21, 2019

(51) Int. Cl.
*G16H 10/60* (2018.01)
*H04N 21/45* (2011.01)
(Continued)

(52) U.S. Cl.
CPC .............. *G16H 10/60* (2018.01); *G06F 3/011* (2013.01); *G06F 3/015* (2013.01); *G16H 40/63* (2018.01);
(Continued)

(58) Field of Classification Search
CPC combination set(s) only.
See application file for complete search history.

(56) References Cited

U.S. PATENT DOCUMENTS 7,354,380 B2 4/2008 Volpe, Jr.
8,702,238 B2 * 4/2014 Berry et al.
(Continued)

FOREIGN PATENT DOCUMENTS

CN 105431851 A 3/2016
CN 106060226 A 10/2016
(Continued)

OTHER PUBLICATIONS

Boulos, Maged N. Kamel, et al. "How Smartphones are Changing the Face of Mobile and Participatory Healthcare: an Overview, with Example from eCAALYX," BioMedical Engineering Outline 2011, 10:24, http://www.biomedical-engineeering-online.com/content/10/1/24, 2011.

(Continued)

*Primary Examiner* — Michael Tomaszewski
*Assistant Examiner* — William T. Monticello
(74) *Attorney, Agent, or Firm* — Patterson + Sheridan, LLP

(57) ABSTRACT

A process receives, with a receiver, health and wellness data of a user that is sensed by one or more sensors during consumption by the user of media content. Further, the process receives, with the receiver, health and wellness data of the user that is determined by a healthcare provider during an event that is distinct from the consumption of the media content. In addition, the process aggregates, with a processor, the health and wellness data of the user that is sensed and the health and wellness data of the user that is determined by the health care provider into an aggregated health and wellness data model. The process also determines, with the processor, one or more optimal audio/visual device settings based on the aggregated health and wellness data model.

22 Claims, 13 Drawing Sheets

(51) Int. Cl.
*G16H 40/63* (2018.01)
*G06F 3/01* (2006.01)
*H04N 21/475* (2011.01)
*H04N 21/41* (2011.01)
*H04N 21/442* (2011.01)
*G16H 40/67* (2018.01)

(52) U.S. Cl.
CPC ......... *G16H 40/67* (2018.01); *H04N 21/4126* (2013.01); *H04N 21/44222* (2013.01); *H04N 21/4532* (2013.01); *H04N 21/4758* (2013.01); *G06F 2203/011* (2013.01)

(56) References Cited

U.S. PATENT DOCUMENTS

| | | |
|---|---|---|
| 8,905,927 B2 | 12/2014 | Cheung Hyen et al. |
| 9,511,259 B2 | 12/2016 | Mountain |
| 9,693,711 B2 | 7/2017 | Yuen et al. |
| 10,033,780 B2* | 7/2018 | Siminoff et al. |
| 10,205,988 B1* | 2/2019 | Waterman et al. |
| 2003/0126593 A1 | 7/2003 | Mault |
| 2007/0071262 A1 | 3/2007 | Rass |
| 2011/0125777 A1 | 5/2011 | Begeja et al. |
| 2011/0166937 A1 | 7/2011 | Bangera et al. |
| 2012/0110602 A1 | 5/2012 | Sanders |
| 2012/0253847 A1 | 10/2012 | Dell'Anno et al. |
| 2014/0207950 A1* | 7/2014 | Badiee |
| 2014/0223462 A1* | 8/2014 | Aimone et al. |
| 2015/0074232 A1* | 3/2015 | Phillips et al. |
| 2015/0228245 A1 | 8/2015 | Lee et al. |
| 2015/0290419 A1 | 10/2015 | Kare et al. |
| 2015/0363554 A1* | 12/2015 | Farrell et al. |
| 2016/0019360 A1* | 1/2016 | Pahwa et al. |
| 2016/0055420 A1* | 2/2016 | Karanam et al. |
| 2017/0071537 A1 | 3/2017 | Jain et al. |
| 2017/0220570 A1* | 8/2017 | Tilaye et al. |
| 2017/0262164 A1* | 9/2017 | Jain et al. |
| 2018/0070136 A1* | 3/2018 | McCarthy |
| 2019/0043283 A1* | 2/2019 | Hyde et al. |
| 2019/0313158 A1* | 10/2019 | Liang et al. |

FOREIGN PATENT DOCUMENTS

| | | |
|---|---|---|
| CN | 106462928 A | 2/2017 |
| EP | 3001422 | 3/2016 |
| EP | 3001422 A1 | 3/2016 |
| JP | 2008-225794 | 9/2008 |
| KR | 10-2007-0041079 | 4/2007 |
| WO | 2010020924 | 2/2010 |

OTHER PUBLICATIONS

Chew, Ivan, et al., "Smart Lighting: The Way Forward? Reviewing the Past to Shape the Future," School of Engineering, Monash University, Malaysia, 47500 Selangor, Malaysia, http://dx.doi.org/10.1016/j.enbuild.2017.04.083, 2017.

Lisetti, C., et al., "Developing Multimodal Intelligent Affective Interfaces for Tele-home Health Care," International Journal of Human-Computer Studies, 59, No. 1-2, www.sciencedirect.com, Jan. 20, 2003.

Stach, Tadeusz, et al., "Heart Rate Control of Exercise Video Games," https://www.researchgate.net/publication/221474925, Jan. 2009.

Chinese Office Action for Application No. 201810903023.1 dated Apr. 12, 2021.

* cited by examiner

GENERAL HEALTH INFORMATION

PRESCRIPTION VALUE:

LEFT EYE    RIGHT EYE

◉ Farsighted

◉ Secondary

*Examples of related pre-existing health conditions that will be useful in determining A/V settings*

LIST CURRENT MEDICATION:

*List of possible types based for certain pre-existing condition*

PRE-EXISITING CONDITIONS

◉ EYE GLASSES:    ◉ Nearsighted    ◉ Farsighted

◉ HYPERTENSION:    ◉ Primary    ◉ Secondary

◉ ON MEDICATION:

◉ HEARING LOSS:
- ◉ Mild
- ◉ Moderate
- ◉ Severe
- ◉ Profound

◉ COLOR BLIND:
- ◉ Trichromacy
- ◉ Anomalous Trichromacy
- ◉ Dichromacy
- ◉ Monochromacy ◉ DIABETIC RETINOPATHY:
- ◉ Nonproliferative Diabetic Retinopathy (NPDR)
- ◉ Proliferative Diabetic Retinopathy (NPDR)

◉ PHOTOSENSITIVE:

◉ PHOTOPHOBIA:

FIG. 5B

USER HEALTH INFORMATION

UPDATED: 5/25/2017    BY: Dr. Name

◎ IMPORT FROM USER HEALTH PROFILE
◎ ENTER MANUAL INFORMATION

PRE-EXISTING CONDITIONS

| EYE GLASSES: | ◎ Nearsighted | ◎ Farsighted | PRESCRIPTION VALUE: |
|---|---|---|---|
| | | | LEFT EYE    RIGHT EYE |

◎ HYPERTENSION: ◎ Primary  ◎ Secondary

◎ ON MEDICATION: LIST CURRENT MEDICATION:

◎ HEARING LOSS: ◎ Mild  ◎ Moderate  ◎ Severe  ◎ Profound

◎ COLOR BLIND: ◎ Trichromacy  ◎ Anomalous Trichromacy  ◎ Dichromacy  ◎ Monochromacy ◎ DIABETIC RETINOPATHY: ◎ Nonproliferative Diabetic Retinopathy (NPDR)  ◎ Proliferative Diabetic Retinopathy (NPDR)

◎ PHOTOSENSITIVE:
◎ PHOTOPHOBIA:

*List of possible types based for certain pre-existing condition*

*Examples of related pre-existing health conditions that will be useful in determining A/V settings*

FIG.6B

SYSTEM FOR ADJUSTING AN AUDIO/VISUAL DEVICE BASED ON HEALTH AND WELLNESS DATA

BACKGROUND

1. Field

This disclosure generally relates to the field of audio/visual ("A/V") devices. More particularly, the disclosure relates to adjustments to A/V device user preferences based on health and wellness data.

2. General Background

Even though use of an increasing number of technology-based devices (e.g., televisions, smart phones, tablet devices, etc.) has provided numerous benefits, many of these devices also pose certain health concerns to users. For instance, users may suffer from nausea, eyestrain, headaches, motion sickness, etc. when consuming A/V content. Users often do not know the cause of such adverse effects (i.e., A/V content consumption) until after the media content has been consumed; even then, many users typically guess as to the cause of their discomfort. As a result, increased usage of conventional A/V devices may lead to a corresponding increase in adverse health effects.

SUMMARY

In one aspect, a computer program product comprises a non-transitory computer readable storage device having a computer readable program stored thereon. The computer readable program when executed on a computer causes the computer to receive, with a receiver, health and wellness data of a user that is sensed by one or more sensors during consumption by the user of media content. Further, the computer is caused to receive, with the receiver, health and wellness data of the user that is determined by a healthcare provider during an event that is distinct from the consumption of the media content. In addition, the computer is caused to aggregate, with a processor, the health and wellness data of the user that is sensed and the health and wellness data of the user that is determined by the health care provider into an aggregated health and wellness data model.

The computer is also caused to determine, with the processor, one or more optimal A/V device settings based on the aggregated health and wellness data model. In addition, the computer is caused to send, with the processor, the one or more optimal A/V device settings to an A/V device so that the A/V device adjusts one or more A/V device settings based on the one or more optimal A/V device settings. In another aspect, a process is provided to perform the functionality of the computer program product.

In yet another aspect, a computer product comprises a non-transitory computer readable storage device having a computer readable program stored thereon. The computer readable program when executed on a computer causes the computer to receive, at an A/V device from a server, one or more optimal A/V device settings that are determined by the server based on an aggregated health and wellness data model. The aggregated health and wellness data model includes data that is sensed by one or more sensors during consumption by the user of media content at the A/V device in addition to health and wellness data of the user that is determined by a healthcare provider during an event that is distinct from the consumption of the media content.

Further, the computer is caused to adjust, at the A/V device, a user profile of the user based on the one or more optimal A/V device settings. In addition, the computer is caused to provide, at the A/V device, additional media content to the user based on the adjusted user profile.

BRIEF DESCRIPTION OF THE DRAWINGS

The above-mentioned features of the present disclosure will become more apparent with reference to the following description taken in conjunction with the accompanying drawings, wherein like reference numerals denote like elements and in which:

FIG. 5B illustrates the GUI depicting data fields for a user's general health information such as pre-existing conditions, any current medications, etc.

FIG. 6B illustrates the GUI depicting data fields for a user's general health information such as pre-existing conditions, any current medications, etc. as determined by the health care provider rather than the user.

DETAILED DESCRIPTION

A configuration for adjusting an A/V device based on health and wellness data is provided. The configuration allows for an automatic adjustment of user preferences for the A/V device based on a variety of health and wellness data. As a result, potential adverse health effects are minimized for a user by automatically adjusting the user preferences for an A/V device based on the health and wellness data for that particular user. Further, those customized user preferences may be shared amongst multiple devices so that the user can conveniently access each A/V device and consume media content according to the optimal device settings for that user; as a result, adverse health effects are minimized on devices that may not have participated in sensing the adverse health effects.

Figure 1:
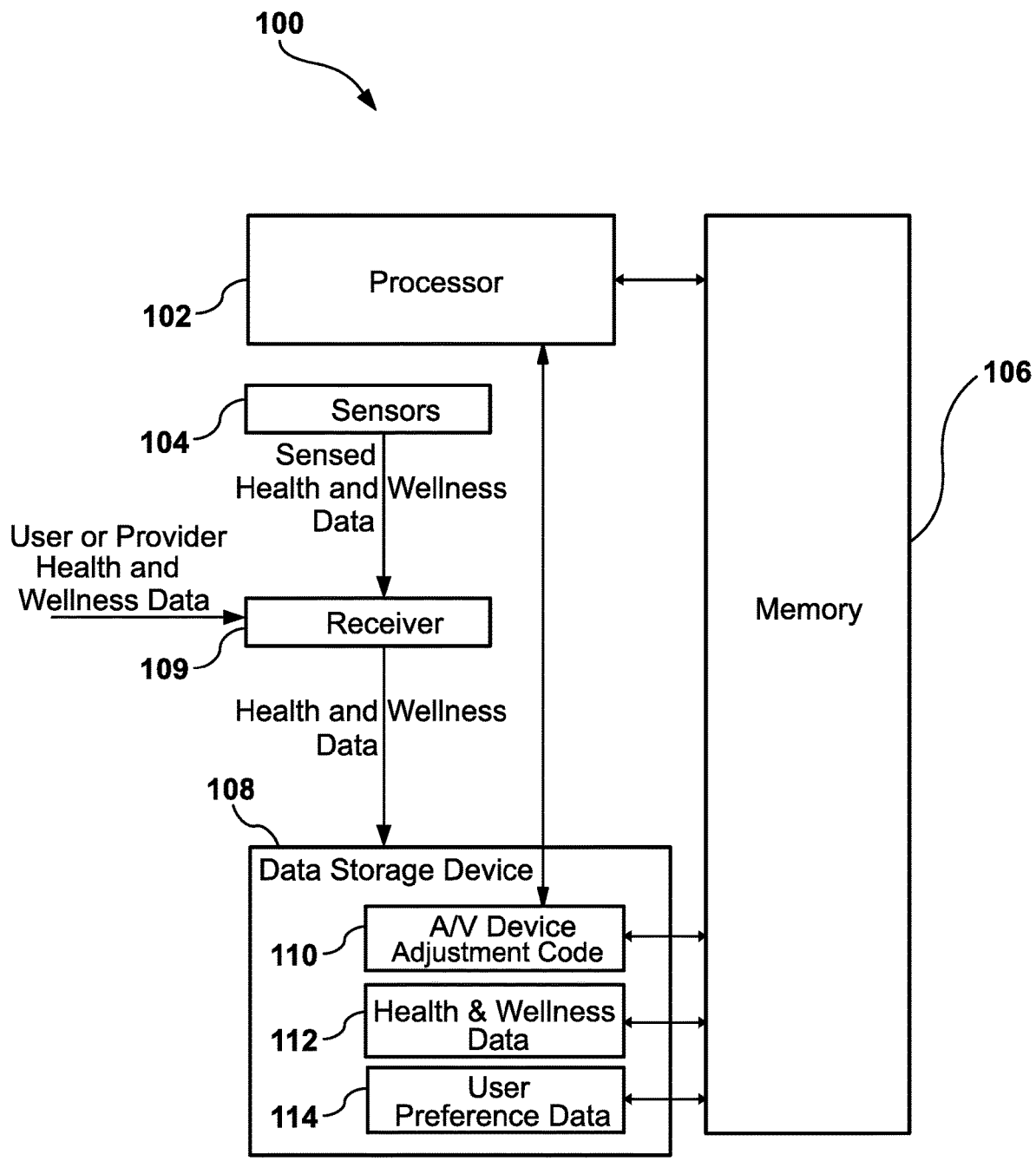
FIG. 1 illustrates an A/V device adjustment system that is used to adjust A/V device settings based on health and wellness data for a corresponding user.

FIG. 1 illustrates an A/V device adjustment system 100 that is used to adjust A/V device settings based on health and wellness data for a corresponding user. In one aspect, the A/V device adjustment system 100 is a server that remotely adjusts user preferences for various A/V devices. Accordingly, the A/V device adjustment system 100 is illustrated herein as server, but can be implemented in a variety of devices and configurations. For example, the A/V device being operated by the user may act as the A/V device adjustment system 100. As yet another example, a peer-to-peer configuration may be implemented such that one or more of the A/V devices acts as the A/V device adjustment system 100.

As illustrated, the A/V device adjustment system 100 comprises a processor 102, a memory 106, e.g., random access memory ("RAM") and/or read only memory ("ROM"), a data storage device 108, and various sensors 104. The sensors 104 may sense various health and wellness properties of one or more users that are consuming an A/V device. Examples of the sensors 104 include cameras, biometric sensors, infrared ("IR") head sensors, smart watches, smart glasses, mobile devices, clothes, bracelets, fitness bands, necklaces, drones, and/or any other sensor that may automatically sense biological properties of the user without any manual input from the user. Examples of the sensed health and wellness properties include pulse rate, blood pressure, temperature, pupil dilation, and sweat. The sensors 104 may then provide the sensed health and wellness data to a receiver 109.

Further, additional health and wellness data may also be received independently of that which is sensed from the user. For example, a health care provider may provide data from medical records (e.g., annual checkup) to the receiver 109. In addition, the user may manually input health and wellness data that is observed by the user. The sensed, user provided, and/or health care entity provided health and wellness data may then be stored in the data storage device 108 and/or the memory 106.

In one aspect, the sensors 104 are integrated within the A/V device adjustment system 100. In another aspect, the sensors 104 are not integrated within the A/V device adjustment system 100, but are in operable communication with the A/V device adjustment system 100; such operable communication may be direct and/or indirect communication. For example, a sensor 104 may send data directly to the A/V device adjustment system 100 (e.g., the sensor 104 is in close proximity to the A/V device adjustment system 100), or data may be aggregated via a cloud service from the sensor 104 (e.g., a remote sensor 104) for retrieval by the A/V device adjustment system 100. For instance, a sensor 104 may send the health and wellness data to a receiver 109 of the A/V device adjustment system 100 that may or may not be remotely located from the sensor 104, or the sensor 104 may act as a receiver 109 that is integrated within the A/V device adjustment system 100.

The processor 102 may execute A/V device adjustment code 110 to analyze the health and wellness data 112 aggregated from one or more different sources; as a result of this analysis, the processor 102 may determine an optimal user preference for content consumption. For example, the health and wellness data 112 may indicate that the user has difficulty hearing when the volume is below a particular volume threshold. Further, the health and wellness data 112 may indicate that the user has previously manually adjusted an A/V device to a certain volume. The processor 102 may then execute the A/V device adjustment code 100 to establish or adjust a user preference for volume when consuming media content; that user preference may be based on an average of measurements received from different sources, a weighting performed on different measurements, or a variety of other calculations used to determine an optimal user preference for an A/V device setting to minimize health and wellness adverse effects. The resulting user preference data 114 (e.g., volume, brightness, contrast, etc.) may be stored with the A/V device adjustment code 100 and the health and wellness data 112 in one or more data storage devices 108 and or memory devices 106.

In one aspect, the data storage device 108 loads A/V device adjustment code 110 from a computer readable storage device, e.g., a magnetic or optical drive, diskette, or non-volatile memory, DVD, CD-ROM, etc. The A/V device adjustment code 110 is then operated by the processor 102 in the memory 106 of the A/V device adjustment system 100 to adjust the A/V device settings if the processor 102 determines that a particular A/V device has one or more properties that do not conform with the user preference data 114 that the processor 102 determines to be optimal for a particular user consuming media content. In another aspect, the data storage device 108 is the computer readable storage device. In yet another aspect, the A/V device adjustment code 110 is stored in the memory 106 rather than the data storage device 108. As such, the A/V device adjustment code 110 and associated data structures of the present disclosure may be stored on a computer readable storage device.

The A/V device adjustment system 100 improves the functioning of a computing device by reducing the processing time to provide a customized user experience. In contrast with a manual calibration of a device that provides a user experience, the A/V device adjustment system 100 automatically senses data that may not feasibly be determined through manual calibration. For example, the process of a user attempting to provide manual subjective inputs to adjust a volume setting of an A/V device is ostensibly more time-consuming than the processor 104 obtaining sensed health and wellness data associated with the user and processing those signals to automatically determine whether or not to perform an A/V device adjustment.

Further, the A/V device adjustment system 100 improves the functioning of a computing device via a user preference data model that is built according to the sensed health and wellness data, health and wellness data received from a healthcare provider system, and/or user inputted data via an input device associated with the A/V device. By implementing this particular data model, the A/V device adjustment system 100 allows the processor 104 to have increased flexibility to adjust the A/V device via data that the user may be unaware of.

Although the components of the A/V device adjustment system 100 are illustrated in FIG. 1 as being integrated within one device, the components may alternatively communicate with each other remotely through a network connection. For example, the processor 102 may be stored on a remote server that communicates with the sensors 104 stored in a wearable device worn by the user. Alternatively, the processor 102 may be built into a sensor 104 itself. For example, the processor 102 may be integrated into a sensor 104 of a wearable device (e.g., headset, watch, bracelet, glasses, etc.) or an adjoining apparatus of the wearable device. As yet another example, the processor 102 may be integrated into a wearable device, but the sensor 104 may be a distinct device that communicates, indirectly (through the receiver 109) or directly, with the processor 102. As another example, the sensor 104 may be built into a non-wearable device such as a camera that also has an integrated processor 102 (e.g., to measure pupil dilation and adjust the A/V device settings accordingly).

Figure 2:
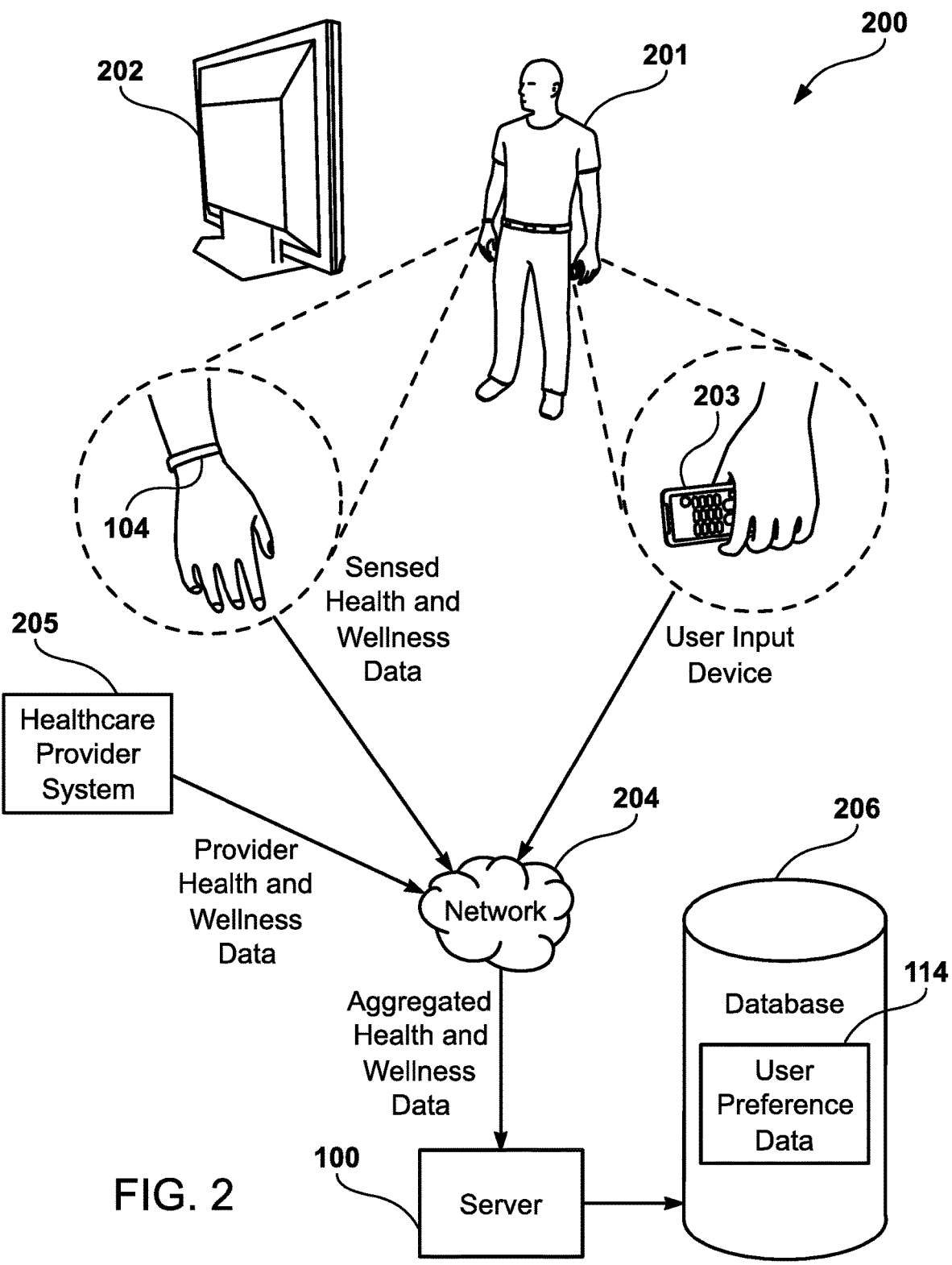
FIG. 2 illustrates an A/V configuration in which the A/V device adjustment system illustrated in FIG. 1 aggregates health and wellness data from different sources.

FIG. 2 illustrates an A/V configuration in which the A/V device adjustment system 100 illustrated in FIG. 1 aggregates health and wellness data from different sources. For illustrative purposes, the A/V device adjustment system 100 is illustrated as a server implementation, but a variety of other types of configurations may be used to implement the A/V device adjustment system 100.

A first possible source of health and wellness data is determined from one or more sensors 104 worn by a user 201 during the consumption of media content on an A/V device such as, for example, a television 202. The consumption of the media content is not limited to viewing on a display screen such as the television 202 as the media consumption may also include listening to an audio experience, playing of a video game, participation in a physical task associated with an A/V device, etc. The one or more sensors 104 (e.g., heart monitor, blood pressure monitor, scale, movement detector, etc.) measure various health and wellness data (e.g., pulse, heart rate, weight, pupil dilation, sweat, etc.) during the media consumption of the content displayed by the television 202 or other A/V device. Accordingly, the one or more sensors 104 measure certain health and wellness data that may not be convenient or feasible for the user 201 to measure during the consumption of the media content. The one or more sensors 104 then send the sensed health and wellness data through a network 204 (e.g., Internet, wireless network, wired network, etc.) to the A/V device adjustment system 100.

Further, a second possible source of health and wellness data may be obtained from a healthcare provider system 205. For instance, a doctor's office, hospital, and/or insurance provider may have medical records associated with the user 201 that was obtained during doctor visits, annual checkups, etc. The healthcare provider system 205 may send such health and wellness data to the A/V device adjustment system 100 so that the A/V device adjustment system 100 may use such data in conjunction with the health and wellness data sensed by the one or more sensors 104.

In addition, a third possible source of health and wellness data may be obtained via a user input device 203. The user 201, or a person trusted by the user 201, may provide manual inputs to the user input device 203 that indicate a user preference for particular A/V device settings (e.g., a particular setting for volume, brightness, contrast, etc.). The user input device 203 may be selected from a variety of devices that control and/or provide input to an A/V device. For example, the user input device 203 may be a remote control, a keyboard, a joystick, a pointing device, etc.

After receiving the health and wellness data from the various sources, the A/V device adjustment system 100 determines one or more optimal user preferences for the user 201. For example, the A/V device adjustment system 100 may determine that the user 201 prefers to listen to content at a particular A/V device volume, but that certain adverse effects result from that preferred volume (e.g., an increase in heart rate detected by the sensors 104) and that the doctor of the user 201 has advised against the user 201 listening to content at that volume. Accordingly, the A/V device adjustment system 100 may adjust the volume setting only as much as necessary to conform to the doctor's recommendation.

Therefore, in one aspect, the A/V device adjustment system 100 implements one or more rules to adjust a setting of an A/V device. The one or more rules dictate the manner in which an A/V device setting is calculated based on different sources of health and wellness data. For example, one set of rules provides that priority is given to one designated source of data, e.g., a doctor over the user 201, in the event of a conflict of data. As another example, another set of rules may average the different designated sources of a data in the event of a conflict of data (i.e., the setting provided by the doctor of the user 201 is averaged with the preferred setting of the user 201). For instance, an average brightness setting may be calculated based upon the doctor's recommended brightness setting and the preferred brightness setting of the user 201. The implementation of such rules allows the A/V device adjustment system 100 to improve the process of determining an A/V device setting for the user 201.

In one aspect, the A/V device adjustment system 100 uses an artificial intelligence ("AI") computer implemented system to implement the one or more rules. Accordingly, the AI may adjust a setting of an A/V device based upon the aggregated health and wellness data meeting certain predefined criteria in addition to resolving conflicts based on one or more prioritization rules.

In another aspect, the A/V device adjustment system 100 stores the user preference data 114 in a database 206. Accordingly, the database 206 may be searched by the A/V device adjustment system 100 or another system to adjust a setting for an A/V device.

Figure 3:
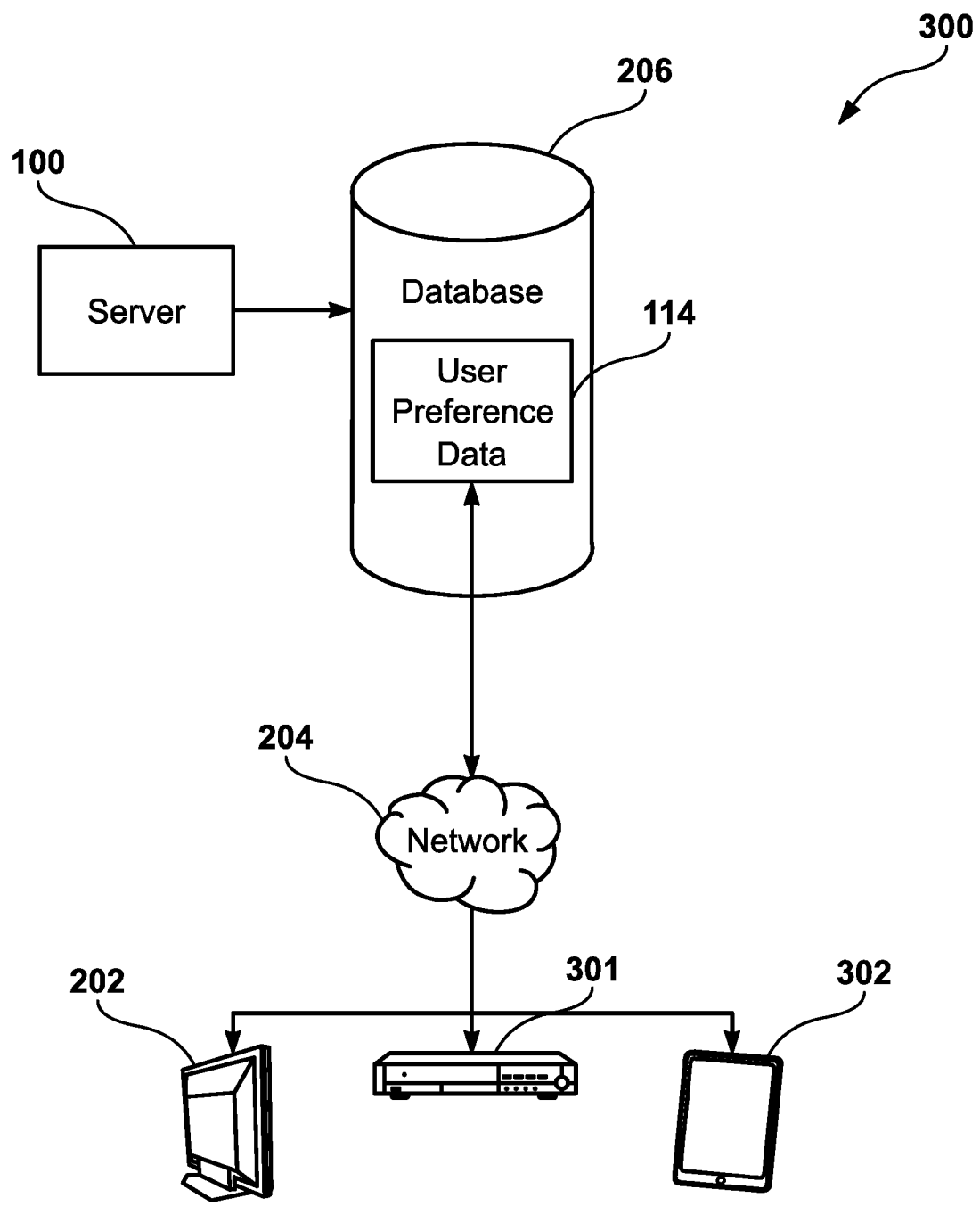
FIG. 3 illustrates a multi-device sharing configuration that allows multiple A/V devices to share the user preferences stored in the database illustrated in FIG. 2.

Further, the A/V device adjustment system 100 may allow the user preference data 114 (FIG. 1) to be shared amongst multiple A/V devices via the database 206. FIG. 3 illustrates a multi-device sharing configuration 300 that allows multiple A/V devices to share the user preference data 114 stored in the database 206 illustrated in FIG. 2. Subsequent to generation of the user preference data 114 by the A/V device adjustment system 100, the database 206 allows multiple A/V devices used by the user 201 to access the same user preference data 114 that may have been generated during the consumption of content by the user 201 with a different A/V device. Rather than having the user 201 subjectively approximate the user preference data 114 in a manner that is inaccurate, the database 206 allows for an automatic update of the user preferences 114 amongst multiple A/V devices used by the user 201.

For example, the user 201 may typically consume media content on the television 202 (e.g., smart television), a DVD player 301, and a tablet device 302. After the database 206 stores the user preference data 114 (FIG. 1) generated by the A/V device adjustment system 100 during the viewing of media content on the television 202, the A/V devices settings of the television 202 in addition to A/V device settings of devices not consumed during the generation of the user preference data 114 (e.g., the DVD player 301 and the tablet device 302) may be adjusted based on those user preferences 114.

By allowing for remote access to the user preference data 114 (FIG. 1) by devices that were not used to consume the media content, the A/V device adjustment system 100 further improves the functionality of a computing device; such sharing of user preferences allows multiple A/V devices to adjust A/V device settings without performing the computations for determining the one or more optimal A/V device settings for the user 201.

Further, in one aspect, the A/V device adjustment system 100 illustrated in FIG. 1 uses the processor 102 to execute the A/V device adjustment code 110 so that the processor 102 translates the user preference data 114 into a corresponding user interface for each of the A/V devices 202, 301, and 302 (FIG. 3) used by the user 201 to consume media content. In other words, each of the A/V devices 202, 301, and 302 may have different code, configuration parameters, designated labels, etc. for adjusting the device parameters for each of the corresponding A/V devices 202, 301, and 302. The processor 102 may translate the user preference data 114 into code, configuration parameters, designated labels, etc. recognizable and executable by each of the A/V devices 202, 301, and 302 so that the corresponding device settings may be adjusted on the respective devices.

Figure 4:
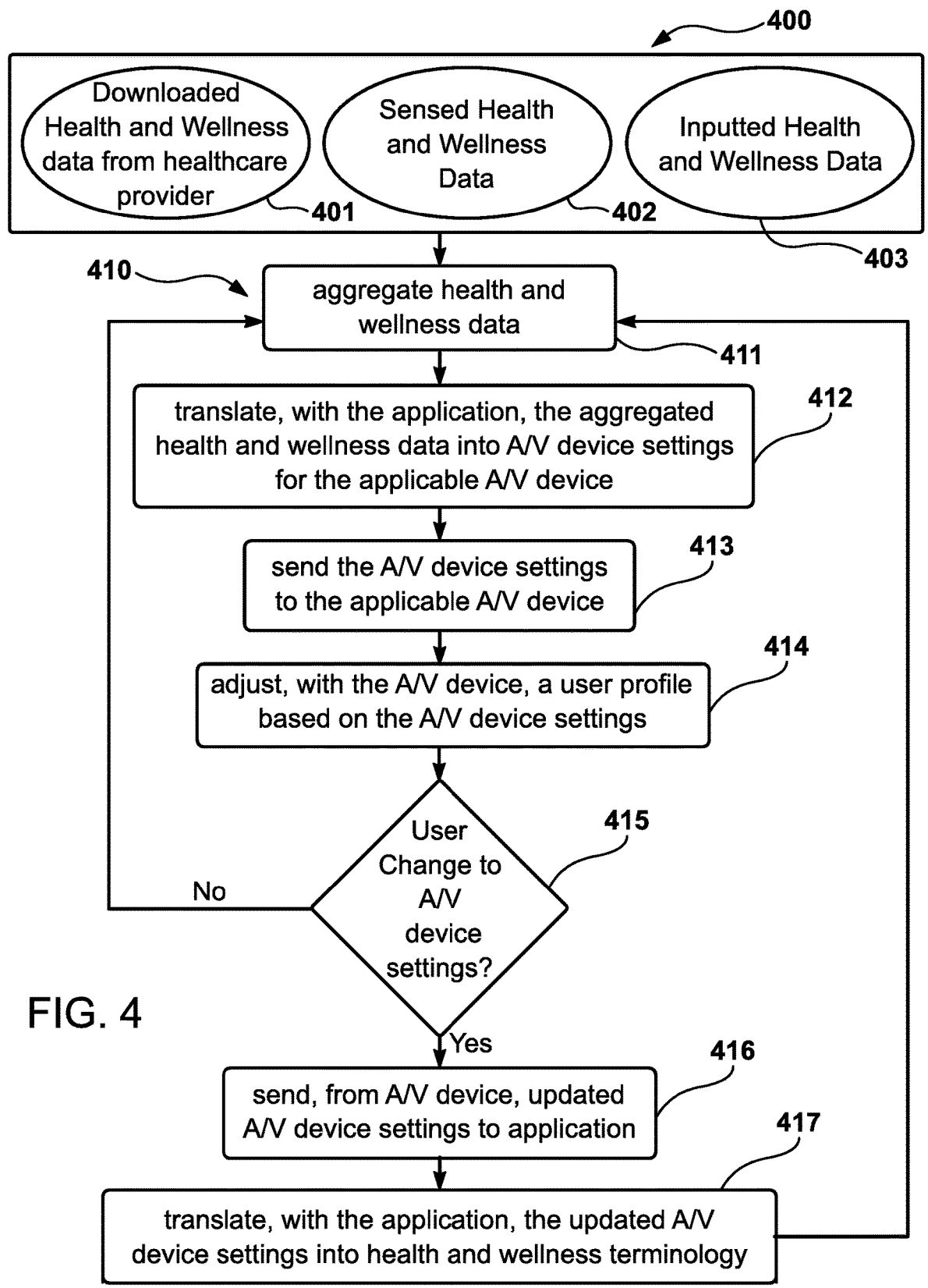
FIG. 4 illustrates a health and wellness data model that is used by a process to translate the user preference data into A/V device adjustment parameters particular to a given A/V device.

FIG. 4 illustrates a health and wellness data model 400 that is used by a process 410 to translate the user preference data 114 (FIG. 1) into A/V device adjustment parameters particular to a given A/V device. The health and wellness data model 400 may include health and wellness data that is aggregated from one or more different sources. For example, the health and wellness data model 400 may include downloaded health and wellness data 401 from a healthcare provider of the user 201 (FIG. 2), sensed health and wellness data 402 that is sensed via one more sensors 104 (FIG. 1), and/or inputted health and wellness data 403 via that is inputted via one or more user input devices 203 (FIG. 2).

At a process block 411, the process 410 aggregates the health and wellness data from the health and wellness data model 400. Prior to proceeding through the remainder of the process 400 to adjust an A/V device setting, the process 400 may analyze the aggregated health and wellness data to determine if any of the sources of the data model 400 should receive any of the aggregated health and wellness data for further review. For example, the sensed health and wellness data 402 may indicate a physical condition of the user 201 (FIG. 2) that was not previously found by the healthcare provider of the user 201. Accordingly, the A/V device adjustment system 100 (FIG. 1) may send that particular data to the healthcare provider 201 for review prior to adjusting a setting of the A/V device for the user 201.

Further, at a process block 412, the process 410 translates, with an application, the aggregated health and wellness data into A/V device settings for the applicable A/V device. For example, an application may be stored on a server that implements the A/V device adjustment system 100 illustrated in FIGS. 1-3. The application may access the database 206 to obtain the generated user preference data 114. In addition, at a process block 413, the process 410 sends the A/V device settings to the applicable A/V device.

At a process block 414, the A/V device receives the A/V device settings from the application and adjusts a user profile for the user 201 (FIG. 2) based on the A/V device settings. If a user profile has not been generated yet for the user 201, the A/V device may generate a user profile at that time.

Further, the process 410 advances to a decision block 415. At the decision block 415, the process 410 determines if the user 201 manually adjusted the recommended A/V device settings. If the user 201 has not manually changed any of the recommended A/V device settings, the process 410 returns to the process block 411 to aggregate any further health and wellness data that is subsequently received from the data model 400.

At the decision block 415, if the user 201 has manually changed any of the recommended A/V device settings, the process 410 proceeds to a process block 416 to send updated A/V device settings from the A/V device to the application. Further, at a process block 417, the process 410 translates, with the application, the updated A/V device settings into health and wellness terminology. The process 410 then returns to the process block 411 to aggregate the updated A/V device settings into the aggregated health and wellness data. The process 410 may also send the updated health and wellness terminology to the healthcare provider of the user 201. In other words, the process 410 provides a feedback loop to adjust the settings of an A/V device based on the monitored health and wellness data of the user 201 in addition to monitoring the response of the user 201 to those recommended A/V device settings.

Figure 5A:
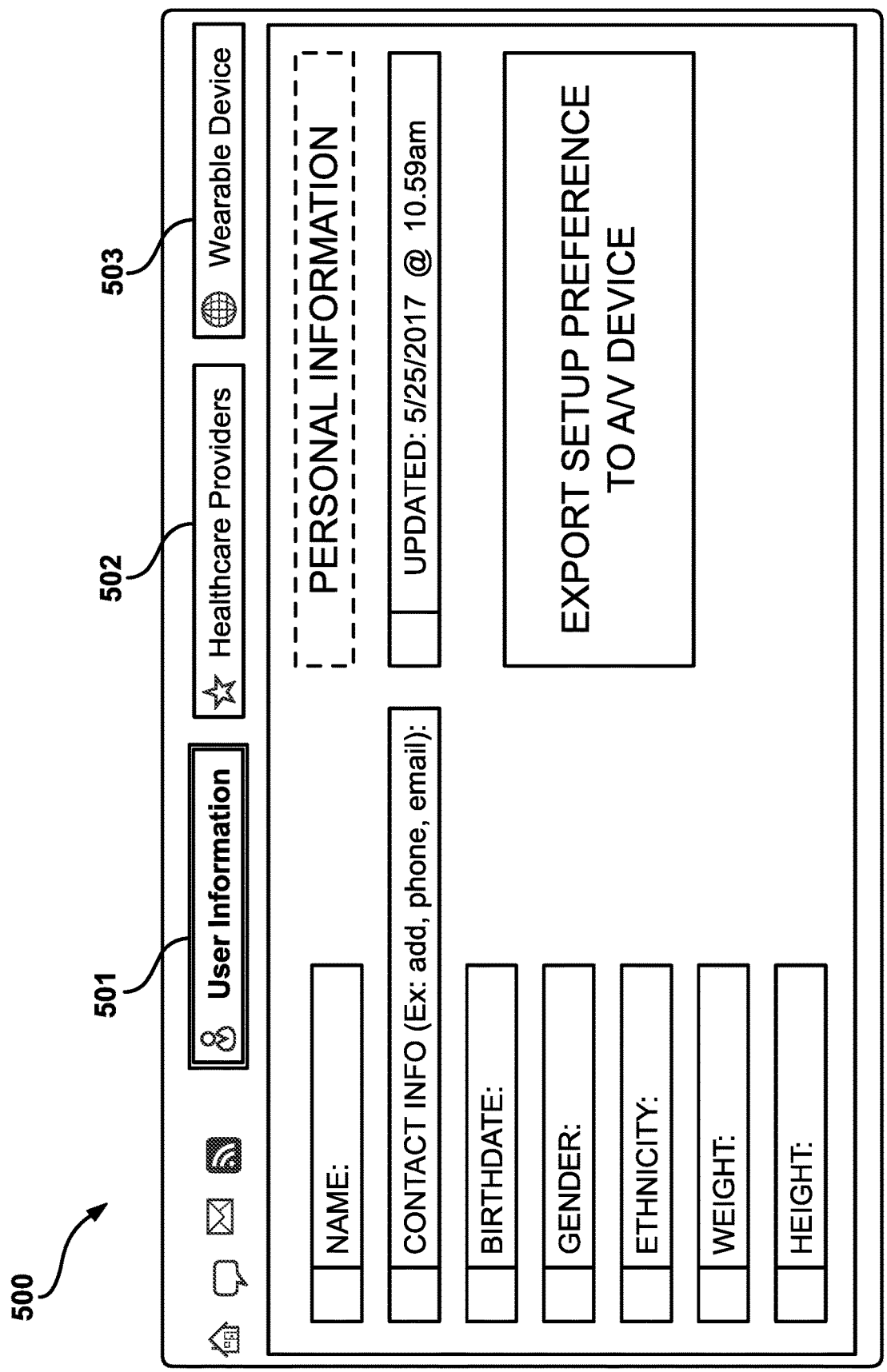
FIG. 5A illustrates a graphical user interface ("GUI") depicting data fields for a user's personal information such as name, contact information, birthdate, gender, weight, and height.
Figure 5C:
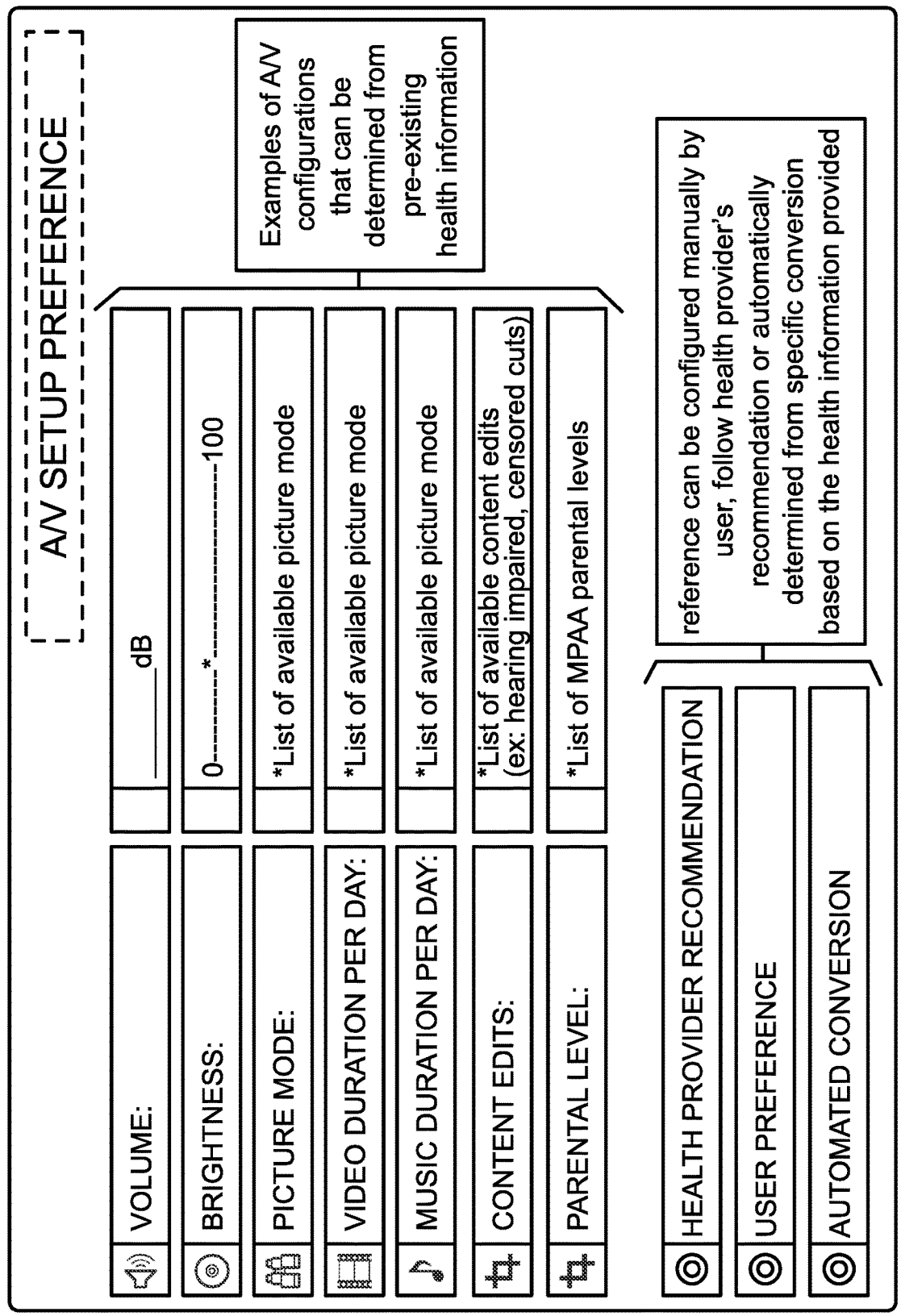
FIG. 5C illustrates the GUI depicting data fields for user's personal preference for an A/V device configuration.

The health and wellness data that is provided to the receiver 109 of FIG. 1 may be inputted via various GUIs. For example, the application discussed with respect to FIG. 4 may be accessible via such GUIs. FIGS. 5A-5C illustrate examples of GUI displays in which a user may enter health and wellness data to be sent to the receiver 109 of FIG. 1. The GUIs may be displayed by the application via a computing device (e.g., desktop computer, laptop, smartphone, tablet device, smartwatch, etc.). Once logged into the application, the user (or trusted entity) can enter personal information, general health information, and personal preferences. The user 201 may export the setup preferences determined from the health and wellness profile to various A/V devices so that all of the A/V devices share the same user profile.

FIG. 5A illustrates a GUI 500 from which different sources (e.g., user, healthcare provider, or wearable device) of health and wellness information may provide one or more inputs via various data fields. For instance, one of a variety of source buttons such a user information source button 501, a healthcare provider source button 502, and a wearable device button 503 may be selected for health and wellness data input. As an example, selection of the user information source button 501 (as highlighted in FIG. 5A) generates one or more forms with one or more data fields from which the user 201 may enter data.

In particular, FIG. 5A illustrates the GUI 500 depicting data fields for a user's personal information such as name, contact information, birthdate, gender, weight, and height. Further, FIG. 5B illustrates the GUI 500 depicting data fields for a user's general health information such as pre-existing conditions, any current medications, etc. In addition, FIG. 5C illustrates the GUI 500 depicting data fields for user's personal preferences for an A/V device configuration. For example, the user 201 may select a preference for volume, brightness, picture mode video duration per day, music duration per day, content edits, and parental level. Further, the user 201 may specify a rule that the A/V device adjustment system 100 uses to prioritize one source of health and wellness data over another. For instance, the user 201 may specify that the A/V device adjustment system 100 should prioritize the health provider recommendation, the user preference, or an automated conversion (e.g., via use of the AI) to determine optimal health and wellness data based on the aggregated health and wellness data.

Figure 6A:
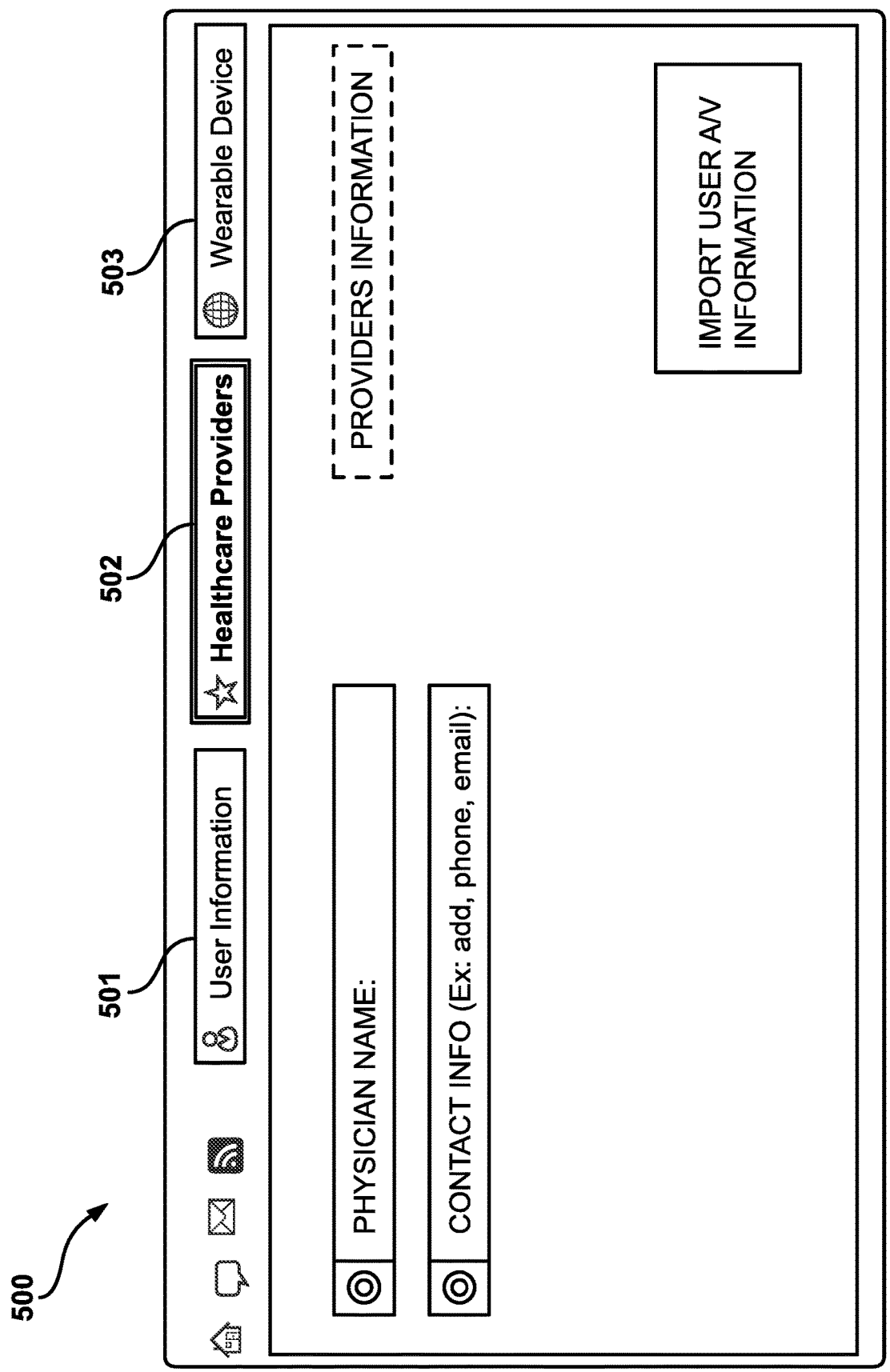
FIG. 6A illustrates the healthcare provider source button of the GUI being highlighted.
Figure 6C:
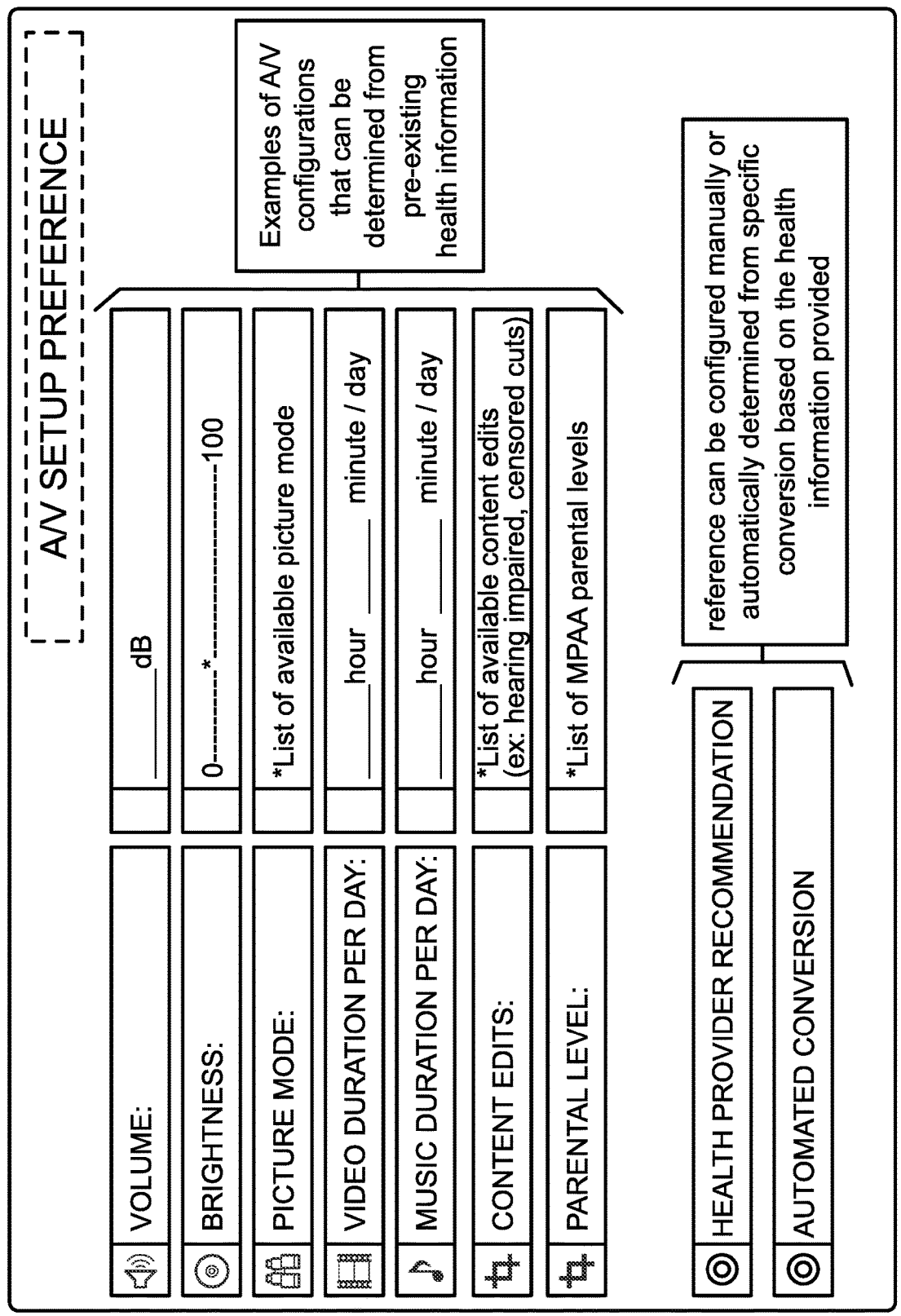
FIG. 6C illustrates the GUI depicting data fields for the health care provider's recommended preferences for an A/V device configuration.

Further, FIGS. 6A-6C illustrate the GUI 500 depicting corresponding data fields to that illustrated in FIGS. 5A-5C when the health care provider has logged into the application to enter health and wellness data for the user 201. Accordingly, FIG. 6A illustrates the healthcare provider source button 502 of the GUI 501 being highlighted.

In particular, FIG. 6A illustrates the GUI 500 depicting data fields for a health care provider's name, contact information, etc. Further, FIG. 6B illustrates the GUI 500 depicting data fields for a user's general health information such as pre-existing conditions, any current medications, etc. as determined by the health care provider rather than the user 201. Such data may be manually inputted by the health care provider via the application or may be imported by the application from the health care provider's system. Further, the health care provider's system may export the data from the application to the health care provider's system so that the health care provider is aware of health and wellness data that was not gathered by the health care provider (e.g., health and wellness data sensed by the sensor 109 or manually inputted by the user 201 during consumption of media content).

In addition, FIG. 6C illustrates the GUI 500 depicting data fields for the health care provider's recommended preferences for an A/V device configuration. For example, a doctor may select a preference for volume, brightness, picture mode video duration per day, music duration per day, content edits, and parental level for the user 201. Further, the health care provider may specify a rule that the A/V device adjustment system 100 uses to prioritize one source of health and wellness data over another. For instance, the health care provider may specify that the A/V device adjustment system 100 should prioritize the health provider recommendation or an automated conversion (e.g., via use of the AI) to determine optimal health and wellness data based on the aggregated health and wellness data.

Figure 7A:
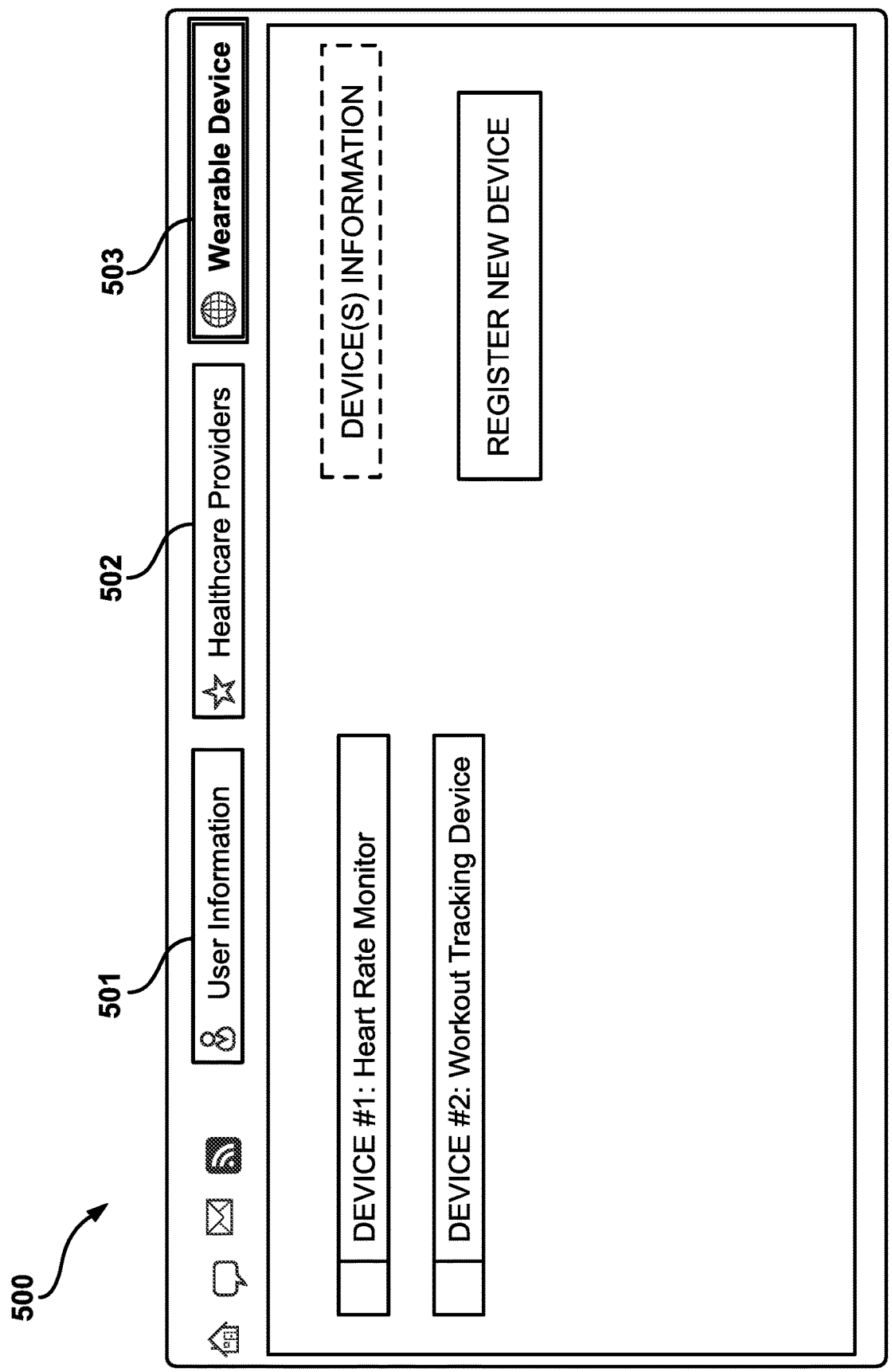
FIG. 7A illustrates the wearable device button of the GUI being highlighted.
Figure 7B:
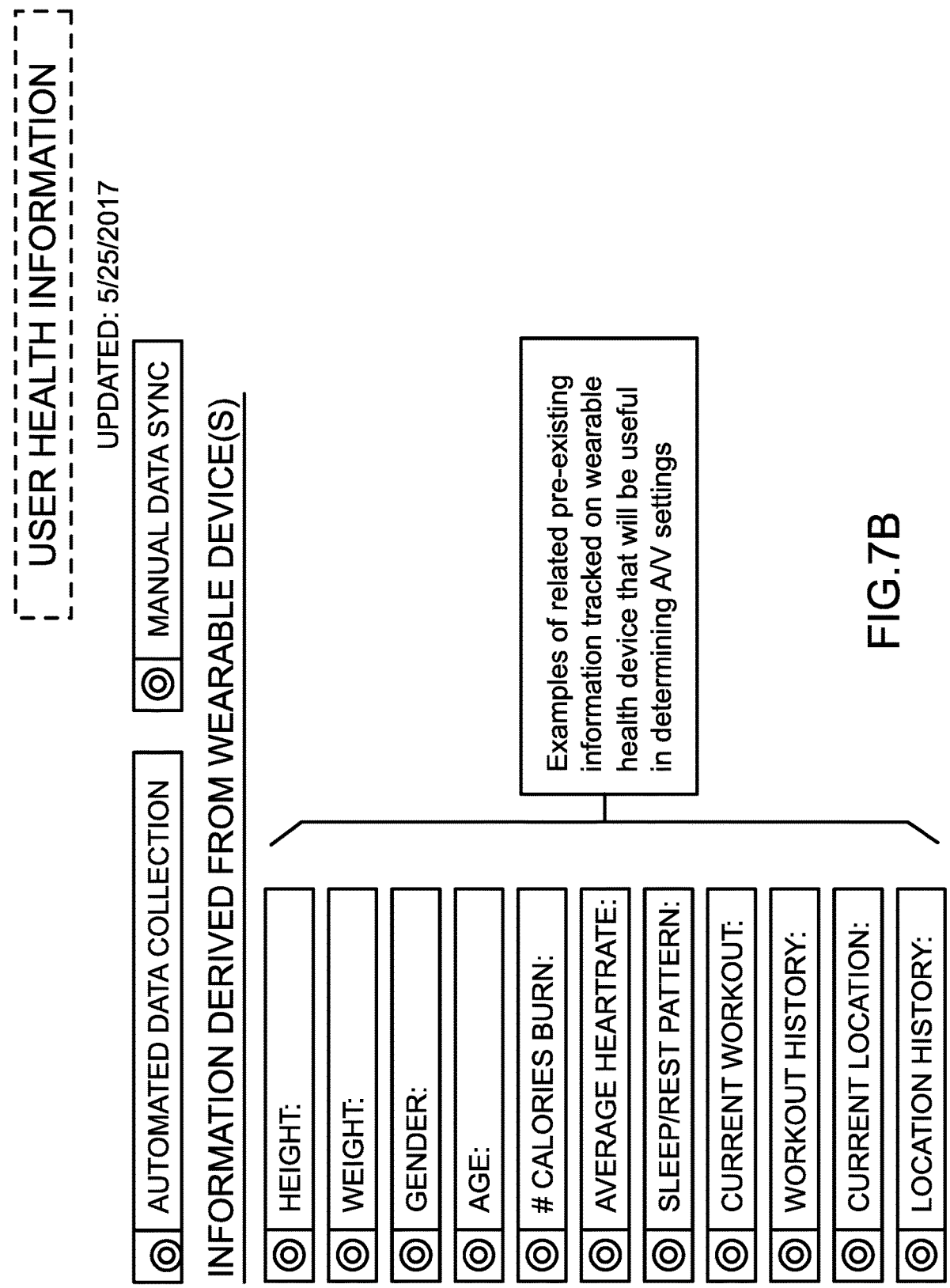
FIG. 7B illustrates the GUI depicting data fields that may be selected by the user (or trusted entity) to track the activity of the user.
Figure 7C:
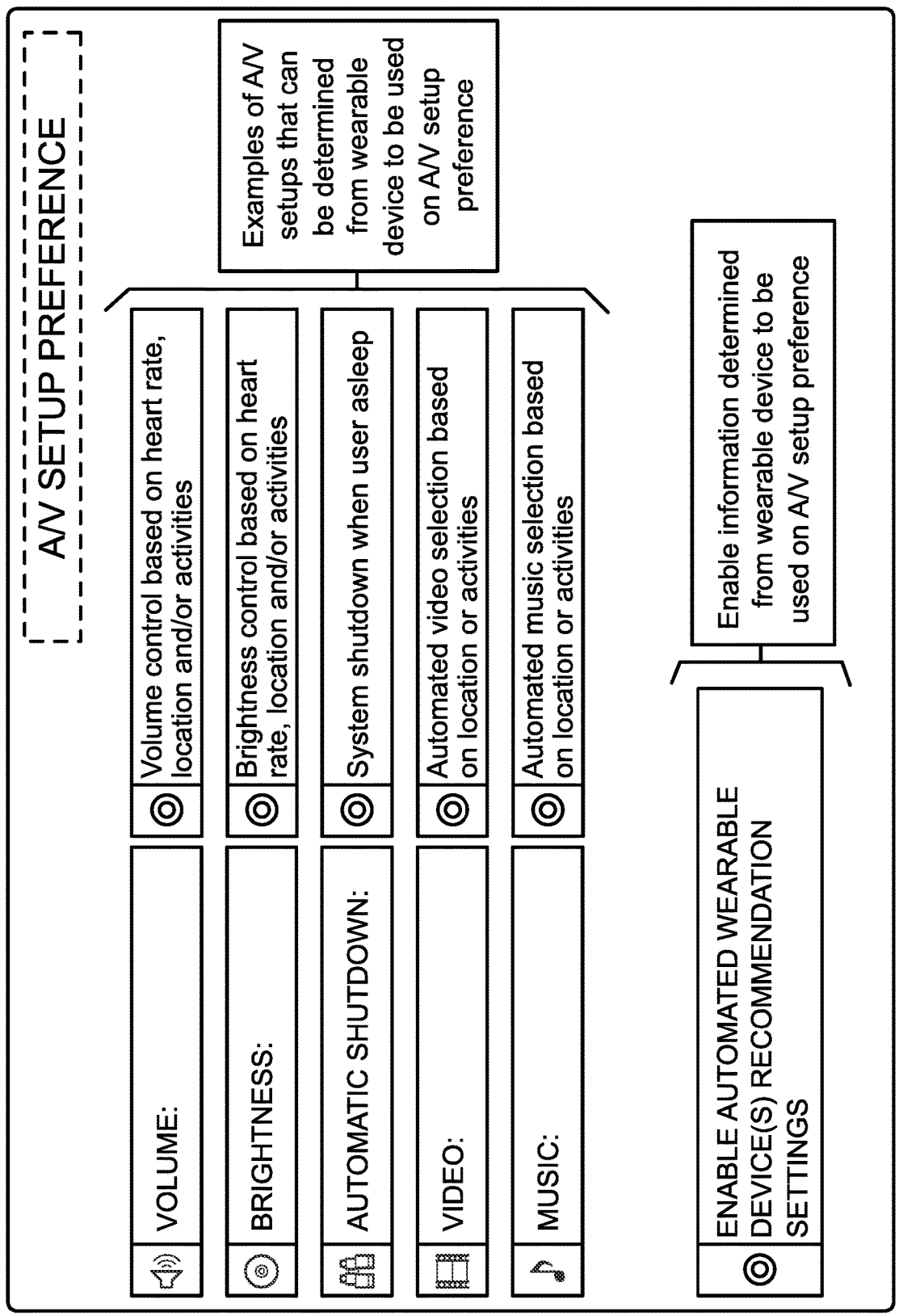
FIG. 7C illustrates recommended user preferences determined from the wearable device.

In addition, FIGS. 7A-7C illustrate the GUI 500 depicting corresponding data fields to that illustrated in FIGS. 5A-5C when the user 201 (or trusted entity), during login to the application, enables a wearable device to influence A/V settings via health information gathered by the wearable device 104 (FIG. 1). Accordingly, FIG. 7A illustrates the wearable device button 503 of the GUI 501 being highlighted. The user 201 may register the wearable device 104 (FIG. 1) with the application. Further, the user 201 may configure the application to automatically update health and wellness information directly from the wearable device 104 or manually synchronize the application with the wearable device 104.

In particular, FIG. 7A illustrates the GUI 500 depicting the wearable devices 104 that have been registered with the application. Further, FIG. 7B illustrates the GUI 500 depicting data fields that may be selected by the user 201 (or trusted entity) to track the activity of the user 201. For example, the data fields may include calories burned, average heart rate, sleep/rest pattern, current workout, workout history, current location, location history, etc. In addition, FIG. 7C illustrates recommended user preferences determined from the wearable device 104. For example, the user 201 (or trusted entity) may configure the volume, brightness, etc. to be automatically controlled based on heart rate, location, and/or activities.

The processes described herein may be implemented in a specialized, general, multi-purpose, or single purpose processor. Such a processor will execute instructions, either at the assembly, compiled or machine-level, to perform the processes. Those instructions can be written by one of ordinary skill in the art following the description of the figures corresponding to the processes and stored or transmitted on a computer readable medium. The instructions may also be created using source code or any other known computer-aided design tool. A computer readable medium may be any medium, e.g., computer readable storage device, capable of carrying those instructions and include a CD-ROM, DVD, magnetic or other optical disc, tape, silicon memory (e.g., removable, non-removable, volatile or non-volatile), packetized or non-packetized data through wireline or wireless transmissions locally or remotely through a network. A computer is herein intended to include any device that has a specialized, general, multi-purpose, or single purpose processor as described above. For example, a computer may be a desktop computer, laptop, smartphone, tablet device, set top box, etc.

It is understood that the apparatuses, systems, computer program products, and processes described herein may also be applied in other types of apparatuses, systems, computer program products, and processes. Those skilled in the art will appreciate that the various adaptations and modifications of the aspects of the apparatuses, systems, computer program products, and processes described herein may be configured without departing from the scope and spirit of the present apparatuses, systems, computer program products, and processes. Therefore, it is to be understood that, within the scope of the appended claims, the present apparatuses, systems, computer program products, and processes may be practiced other than as specifically described herein.

We claim:

1. A computer program product comprising a non-transitory computer-readable device having a computer-readable program stored thereon, wherein the computer-readable program when executed on a server causes the server to:

receive first health and wellness data comprising a health measurement of a user that is sensed by one or more sensors of a first audio/visual device during consumption, by the user, of media content;

receive second health and wellness data comprising a recommended playback setting that is determined for the user by a healthcare provider during an event that is distinct from the consumption of the media content;

receive third health and wellness data comprising a playback setting preferred by the user when using the first audio/visual device;

aggregate, by the server, the first health and wellness data, the second health and wellness data, and the third health and wellness data into an aggregated health and wellness data model;

determine, by a processor of the server when executing the computer-readable program, one or more optimal audio/visual device settings based on the aggregated health and wellness data model, including resolving a conflict between the playback setting preferred by the user and the recommended playback setting based on the health measurement; and remotely and automatically cause, by the server via a network, one or more audio/visual device settings of a second audio/visual device to be adjusted based on the one or more optimal audio/visual device settings, wherein based on the adjusted one or more audio/visual device settings, the second audio/visual device outputs additional media content for consumption by the user.

2. The computer program product of claim 1, wherein the first audio/visual device is used by the user during the consumption of the media content when the first health and wellness data is sensed by the one more sensors of the first audio/visual device.

3. The computer program product of claim 1, wherein the server is further caused to store the one or more optimal audio/visual device settings in a database that is accessible by one or more additional audio/visual devices that were not used by the user during the consumption of the media content when the first health and wellness data is sensed by the one more sensors of the first audio/visual device, the one or more additional audio/visual devices including the second audio/visual device.

4. The computer program product of claim 1, wherein the server is further caused to receive, via a user input device separate from the first audio/visual device, one or more user inputs indicating the third health and wellness data during consumption of the media content by the user.

5. The computer program product of claim 4, wherein the server is further caused to aggregate the one or more user inputs into the aggregated health and wellness data model.

6. The computer program product of claim 1, wherein the conflict is resolved according to one or more rules.

7. The computer program product of claim 6, wherein the one or more rules dictate that the second health and wellness data provided by the healthcare provider has priority over the first health and wellness data that is sensed by the one or more sensors of the first audio/visual device.

8. The computer program product of claim 1, wherein the processor further determines the one or more optimal audio/visual device settings by translating the aggregated health and wellness data from health and wellness terminology to audio/visual device settings associated with the second audio/visual device.

9. The computer program product of claim 1, wherein the server is further caused to receive an update to the one or more optimal audio/visual device settings, wherein the update is specified via a user input at the second audio/visual device.

10. The computer program product of claim 9, wherein the server is further caused to translate the one or more optimal audio/visual device settings into updated health and wellness terminology subsequent to updating the one or more optimal audio/visual device settings.

11. The computer program product of claim 10, wherein the server is further caused to send the updated health and wellness terminology to a system associated with the healthcare provider.

12. A method comprising:
receiving first health and wellness data comprising a health measurement of a user that is sensed by one or more sensors of a first audio/visual device during consumption, by the user, of media content;
receiving second health and wellness data comprising a recommended playback setting that is determined for the user by a healthcare provider during an event that is distinct from the consumption of the media content;
receiving third health and wellness data comprising a playback setting preferred by the user when using the first audio/visual device;
aggregating, by a server, the first health and wellness data, the second health and wellness data, and the third health and wellness data into an aggregated health and wellness data model;
determining, by a processor of the server, one or more optimal audio/visual device settings based on the aggregated health and wellness data model, including resolving a conflict between the playback setting preferred by the user and the recommended playback setting based on the health measurement; and
remotely and automatically causing, by the server via a network, one or more audio/visual device settings of a second audio/visual device to be adjusted based on the one or more optimal audio/visual device settings, wherein based on the adjusted one or more audio/visual device settings, the second audio/visual device outputs additional media content for consumption by the user.

13. A computer program product comprising a non-transitory computer readable device having a computer readable program stored thereon, the computer readable program executable to perform an operation comprising:
receiving, at a first audio/visual device and from a server via a network, one or more optimal audio/visual device settings that are determined by the server based on an aggregated health and wellness data model, the aggregated health and wellness data model comprising (i) first health and wellness data comprising a health measurement of a user that is sensed by one or more sensors of a second audio/visual device during consumption, by the user, of media content at the second audio/visual device, (ii) second health and wellness data comprising a recommended playback setting that is determined for the user by a healthcare provider during an event that is distinct from the consumption of the media content, and (iii) third health and wellness data comprising a playback setting preferred by the user when using the second audio/visual device, wherein the one or more optimal audio/visual device settings are determined by the server by resolving a conflict between the playback setting preferred by the user and the recommended playback setting based on the health measurement;
adjusting, at the first audio/visual device, a user profile of the user based on the one or more optimal audio/visual device settings, wherein the user profile is remotely and automatically caused, by the server via the network, to be adjusted, the user profile including one or more audio/visual device settings associated with the first audio/visual device; and
providing, at the first audio/visual device, additional media content to the user based on the adjusted user profile.

14. The computer program product of claim 13, wherein the aggregated health and wellness data model also includes one or more user inputs received via a user input device separate from the first audio/visual device, the one or more user inputs indicating the third health and wellness data during consumption of the media content by the user.

15. The computer program product of claim 13, wherein the conflict is resolved according to one or more rules.

16. The computer program product of claim 15, wherein the one or more rules dictate that the second health and wellness data provided by the healthcare provider has priority over the first health and wellness data that is sensed by the one or more sensors of the second audio/visual device.

17. The computer program product of claim 13, wherein the one or more optimal audio/visual device settings are further determined through a translation of the aggregated health and wellness data from health and wellness terminology to the audio/visual device settings associated with the first audio/visual device.

18. The computer program product of claim 13, wherein the operation further comprises receiving an update to the one or more optimal audio/visual device settings via a user input at the first audio/visual device.

19. The computer program product of claim 18, wherein the operation further comprises:
subsequent to updating the one or more optimal audio/visual device settings, sending the one or more optimal audio/visual device settings to the server so that the server translates the one or more optimal audio/visual device settings into updated health and wellness terminology.

20. The computer program product of claim 19, wherein the updated health and wellness terminology is sent to a system associated with the healthcare provider.

21. The computer program product of claim 1, wherein the one or more audio/visual device settings of the second audio/visual device are adjusted in order to minimize an adverse health effect on the user, wherein the one or more audio/visual device settings of the second audio/visual device are not adjusted based on any health measurement sensed by the second audio/visual device.

22. The computer program product of claim 1, wherein causing the one or more audio/visual device settings to be adjusted comprises sending the one or more optimal audio/visual device settings via the network to the second audio/visual device in order to cause the second audio/visual device to adjust, based on the one or more optimal audio/video device settings, the one or more audio/visual device settings of the second audio/visual device.

\* \* \* \* \*